(12) United States Patent
Slemker et al.

(10) Patent No.: US 6,470,552 B1
(45) Date of Patent: Oct. 29, 2002

(54) METHOD FOR FABRICATING A COSMETIC COVER FOR A PROSTHETIC LIMB

(75) Inventors: Tracy C. Slemker, Clayton; Schott R. Schall, Englewood, both of OH (US)

(73) Assignee: Prosthetic Design, Inc., Clayton, OH (US)

( * ) Notice: Subject to any disclaimer, the term of this patent is extended or adjusted under 35 U.S.C. 154(b) by 150 days.

(21) Appl. No.: 09/668,926

(22) Filed: Sep. 25, 2000

(51) Int. Cl.$^7$ ................................................ B23P 11/02
(52) U.S. Cl. ............................ 29/447; 29/460; 29/557; 623/33; 409/98; 409/131
(58) Field of Search ................... 29/402.06, 402.21, 29/407.05, 447, 460, 525.11, 527.2, 557, 559; 623/33, 34, 35, 36, 37; 409/98, 99, 65, 131, 132

(56) References Cited

U.S. PATENT DOCUMENTS

| | | | |
|---|---|---|---|
| 5,824,111 A | 10/1998 | Schall et al. | 623/33 |
| 5,880,964 A | 3/1999 | Schall et al. | 364/474.01 |
| 5,888,234 A * | 3/1999 | Littig | 623/38 |
| 5,901,060 A | 5/1999 | Schall et al. | 364/468.04 |
| 5,980,803 A | 11/1999 | Slemker et al. | 264/222 |
| 6,033,440 A | 3/2000 | Schall et al. | 623/38 |

* cited by examiner

Primary Examiner—S. Thomas Hughes
Assistant Examiner—Jermie E. Cozart
(74) Attorney, Agent, or Firm—Taft, Stettinius & Hollister LLP (57) ABSTRACT

A mandrel, and a method using a mandrel, for fabricating a cosmetic cover for a prosthetic limb having a socket for placement over a wearer's residual limb and having a component positioned outside, and attached to, the socket through aligned holes of the component and the socket. The mandrel has a mandrel plate attached to a mandrel shaft. The mandrel plate has holes aligned with the holes of the socket so the mandrel plate may be attached to the socket and the component thereby supporting the prosthetic limb. The mandrel shaft is placed in a chuck of a milling machine when the supported prosthetic limb, with an attached cosmetic cover blank, is attached to the mandrel plate, and the outside surface of the cosmetic cover blank is milled to match a mirror image of the wearer's sound limb.

17 Claims, 5 Drawing Sheets

METHOD FOR FABRICATING A COSMETIC COVER FOR A PROSTHETIC LIMB

FIELD OF THE INVENTION

The present invention relates generally to a prosthetic limb, and more particularly to methods and to apparatus for fabricating a cosmetic cover for a prosthetic limb.

BACKGROUND OF THE INVENTION

A prosthetic limb is used to replace an amputated portion of a limb and to help restore the amputee's ability to use the limb. A prosthetic leg for a lower extremity typically will include artificial foot and ankle components coupled to an upright assembly which, in turn, is coupled to a custom-fitted socket assembly. If the amputation is above the knee, the upright assembly typically includes an artificial knee joint. Often, a cosmetic cover is fabricated to cover the prosthetic limb, such as to cover a prosthetic leg from the socket downward to the artificial foot.

In one conventional method for fabricating a cosmetic cover for a prosthetic leg, the artificial foot is first removed. Then, a cosmetic cover blank is obtained having the shape of a tapered cylinder with a constant wall thickness. The cosmetic cover blank is made of a foam material such as PVC (polyvinyl chloride) foam, EVS foam, ethafoam, or polyethylene foam. The cosmetic cover blank is heated to expand to a point where it will slide over the prosthetic limb. It is noted that differing diameters cause the proximal end of the cosmetic cover blank (i.e., the end of the cosmetic cover blank designed to be closest to the residual limb) to expand more than the distal end of the cosmetic cover blank (i.e., the end of the cosmetic cover blank designed to be farthest from the residual limb). Then, the heated and expanded cosmetic cover blank is slid onto the prosthetic leg. The socket has a bonding agent to bond the inside surface of the cosmetic cover blank to the outside surface of the socket, and a vacuum is applied to draw the cover onto the prosthetic leg as it cools. After cooling, the artificial foot is reattached, and the distal surface of the cosmetic cover blank is bonded to the proximal surface of the artificial foot. The cosmetic cover blank is then manually "shaved" to mimic the anatomy of a sound limb using at least the dimensions of the circumference of the ankle and calf section of the amputee's sound leg. A spray skin finish or cosmetic hose is then applied to the covered prosthetic leg. This method is labor intensive.

In another conventional method for fabricating the cosmetic cover for a prosthetic leg, disclosed in U.S. Pat. No. 5,880,964, a computer-aided-design (CAD) system with a digitizing tool is linked to a computer-numerically-controlled (CNC) milling machine. A cosmetic cover blank, or a longitudinal half blank (i.e., a blank cut in two along its longitudinal axis), is obtained. The prosthetic leg is fitted to the wearer's residual leg and is adjusted. The digitizing tool takes measurements of the prosthetic leg, such measurements being used by the CAD system to command the CNC milling machine to carve the inside surface of the cosmetic cover blank. The digitizing tool also takes measurements of the amputee's sound leg, such measurements being used by the CAD system to create a mirror-image leg to command the CNC milling machine to carve the outside surface of the cosmetic cover blank. The carved cosmetic cover blank is then attached to the prosthetic leg. This method requires a new form of cosmetic cover blank that is not presently on the market.

What is needed is a method for fabricating a cosmetic cover for a prosthetic limb which is not labor intensive and which does not introduce unwanted tolerances between the finished cosmetic cover and the prosthetic limb.

SUMMARY OF THE INVENTION

A first method of the invention is for fabricating a cosmetic cover for a prosthetic limb. The prosthetic limb has a socket for placement over a wearer's residual limb and has a component disposed exterior of the socket. The component and the distal end of the socket have alignable holes for attachment of the component to the socket. The method includes several steps. A cosmetic cover blank is attached over the prosthetic limb. A mandrel is obtained having a mandrel shaft and having a mandrel plate which is attached to one end of the mandrel shaft and which has holes matching the holes of the socket. The mandrel plate is positioned inside the socket. The holes of the mandrel plate, the socket, and the component are aligned. The mandrel plate, the socket, and the component are attached together through the holes of the mandrel plate, the socket, and the component. The mandrel shaft is placed in a chuck of a milling machine. Finally, the outside surface of the cosmetic cover blank is milled by the milling machine. Preferably, the mandrel shaft is placed in a chuck of a computer-numerically-controlled milling machine. The method for attaching the cosmetic cover blank to the prosthetic limb may include the steps of heating the cosmetic cover blank to expand it and then sliding the cosmetic cover blank over the prosthetic limb.

A second method of the invention is for fabricating a cosmetic cover of a prosthetic limb. The prosthetic limb has a socket for placement over a wearer's residual limb, has a component located exterior of the socket, and has a lock located interior of the socket. The component and the distal end of the socket have aligned holes, wherein the holes of the component are threaded holes and wherein the lock has threaded bolts. The threaded bolts are rotatable from inside the socket, extend through the holes of the socket, and are engaged with the threaded holes of the component. The method includes several steps. A cosmetic cover blank is attached over the prosthetic limb. A mandrel is obtained having a mandrel shaft and having a mandrel plate which is attached to one end of the shaft and which has holes matching the holes of the socket. The lock is removed from the component and the socket. The removed lock is replaced with the mandrel plate and threaded fasteners which pass through the holes of the mandrel plate and the socket and which engage the threaded holes of the component. The mandrel shaft is placed in a chuck of a milling machine. The outside surface of the cosmetic cover blank is then milled by the milling machine. Preferably, the mandrel shaft is placed in a chuck of a computer-numerically-controlled milling machine.

A first expression of a preferred embodiment of the mandrel of the invention is for supporting, in a milling machine, a cosmetic cover blank attached to a prosthetic limb during milling of an outside surface of the cosmetic cover blank, wherein the prosthetic limb has a socket for placement over a wearer's residual limb and has a component located exterior of the socket and wherein the component and the distal end of the socket have alignable holes for attachment of the component to the socket. The mandrel includes a mandrel shaft and a mandrel plate. The mandrel shaft has a first end for placement in a chuck of the milling machine and has a second threaded end. The mandrel plate has a threaded hole for engagement with the second threaded end of the mandrel shaft and has holes matching the holes of the socket. The mandrel plate is attachable to the component from within the socket through the holes of the mandrel plate, the socket, and the component.

A second expression of a preferred embodiment of the mandrel of the invention is for supporting, in a milling machine, a cosmetic cover blank attached to a prosthetic limb during milling of an outside surface of the cosmetic cover blank, wherein the prosthetic limb has a socket for placement over a wearer's residual limb, has a component located exterior of the socket, and has a lock located interior of the socket. The component and the distal end of the socket have alignable holes, and the holes of the component are threaded holes. The lock has threaded bolts which are rotatable from inside the socket, which are positionable to extend through the holes of the socket, and which are engageable with the threaded holes of the component for attachment of the component to the socket. The mandrel includes a mandrel shaft and a mandrel plate. The mandrel shaft has a first end for placement in a chuck of the milling machine and has a second threaded end. The mandrel plate has a threaded hole for engagement with the second threaded end of the mandrel shaft and has holes matching the holes of the socket. The mandrel plate is attachable to the component from within the socket through the holes of the mandrel plate and the socket and the threaded holes of the component. Preferably, the method for attaching the cosmetic cover blank to the prosthetic limb first includes the sequential steps of fitting the prosthetic limb to the wearer's residual limb, adjusting the prosthetic limb, and removing the prosthetic limb from the wearer's residual limb.

Several benefits and advantages are derived from the invention. In the methods and expressions of a preferred embodiment of the invention, the cosmetic cover blank is attached to the fitted and adjusted prosthetic limb before shaping the outside surface of the cosmetic cover blank. This utilizes some of the same steps (except the carving step) as those conventional methods which heat a cosmetic cover blank, then slide the cosmetic cover blank over the prosthetic limb, and then manually carve the outside surface of the cosmetic cover blank. In the methods and expressions of a preferred embodiment of the invention, the mandrel allows the outside surface of the cosmetic cover blank to be milled by a milling machine while the cosmetic cover blank is attached to the prosthetic limb. This eliminates intensive labor steps compared to those conventional methods which require manually carving of the outside surface of the cosmetic cover blank.

DETAILED DESCRIPTION

Figure 1:
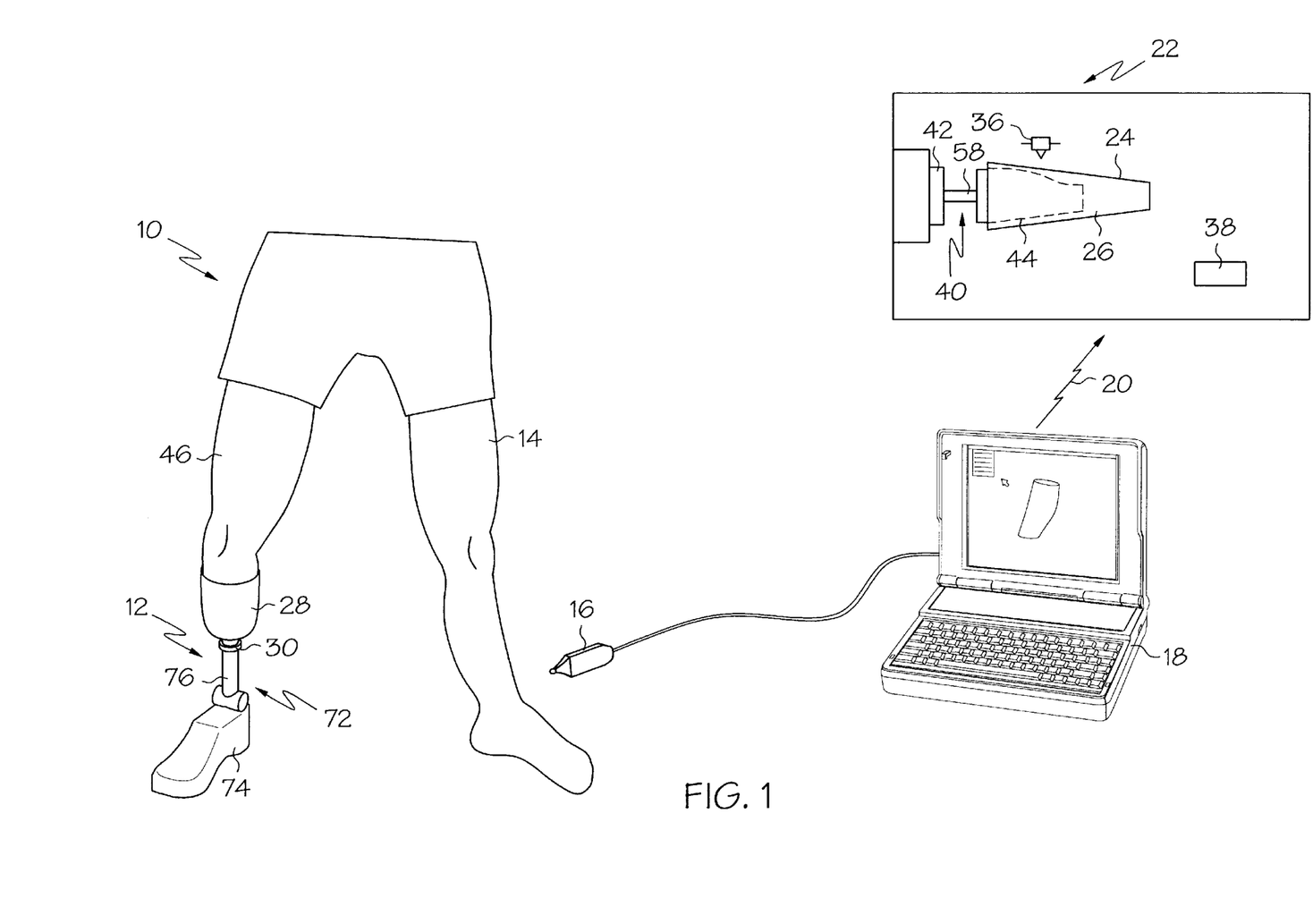
FIG. 1 is a schematic representation of an amputee wearing a prosthetic leg, including a socket and a component, and of a system for milling the outside surface of a cosmetic cover attached to the removed prosthetic leg.

A wearer 10 of a prosthetic limb 12 is shown in FIG. 1 where digital measurements of a sound limb 14 are taken by a digitizing tool 16 and used by a CAD (computer-aided-design) system 18 to command, over a communications link 20, a CNC (computer-numerically-controlled) milling machine 22 to mill the outside surface 24 of a cosmetic cover blank 26 attached to the prosthetic limb 12, such milling occurring after the prosthetic limb 12 has been removed from the wearer 10. The prosthetic limb 12 includes a socket 28 and a component 30 disposed exterior of the socket 28. A conventional socket 28, a conventional component 30, a conventional lock 32, and a conventional inner sleeve 34 are shown in greater detail in FIG. 2. The milling machine 22 includes a cutting tool 36 controlled by a processing unit 38 which receives the digital measurements from the CAD system 18. The removed prosthetic limb and the cosmetic cover blank 26 attached thereto are supported by a mandrel 40 held in a chuck 42 of the milling machine 22. A preferred embodiment of a mandrel 40 of the invention is shown in greater detail in FIG. 3, and a preferred attachment of the mandrel 40 to the prosthetic limb 12 is shown in greater detail in FIG. 4.

A first preferred method of the invention is for fabricating a cosmetic cover 44 (shown in dashed line in FIG. 1) for a prosthetic limb 12. The prosthetic limb 12 has a socket 28 for placement over a wearer's residual limb 46 and has a component 30 (such as, but not limited to, a pyramidal link plate) disposed exterior of the socket 28. The component 30 and the distal end 48 of the socket 28 have a plurality of alignable holes 50 and 52 for attachment of the component 30 to the socket 28. The first preferred method includes steps a) through g). Step a) is portrayed in block 54 of FIG. 5 as "Attach Cosmetic Cover Blank Over Prosthetic Limb". Step a) includes attaching a cosmetic cover blank 26 over the prosthetic limb 12. Step b) is portrayed in block 56 of FIG. 5 as "Obtain Mandrel". Step b) includes obtaining a mandrel 40 having a mandrel shaft 58 and having a mandrel plate 60 attached to one end of the mandrel shaft 58, wherein the mandrel plate 60 has a plurality of holes 62 matching the holes 52 of the socket 28. Step c) is portrayed in block 64 of FIG. 5 as "Dispose Mandrel Plate Inside Socket". Step c) includes disposing the mandrel plate 60 inside the socket 28. Step d) is portrayed in block 66 of FIG. 1 as "Align Holes Of Mandrel Plate, Socket, and Component". Step d) includes aligning the holes 62 of the mandrel plate 60, the holes 52 of the socket 28, and the holes 50 of the component 30. Step e) is portrayed in block 67 of FIG. 1 as "Attach Together Mandrel Plate, Socket, And Component". Step e) includes attaching together the mandrel plate 60, the socket 28, and the component 30 through the holes 62, 52, and 50 of the mandrel plate 60, the socket 28, and the component 30. Step f) is portrayed in block 68 of FIG. 5 as "Dispose Mandrel Shaft In Chuck Of Milling Machine". Step f) includes disposing the mandrel shaft 58 in a chuck 42 of a milling machine (such as, but not limited to, a CNC milling machine 22). For purposes of describing the invention, the terminology "milling machine" includes all cutting machines known by any name (e.g., lathes, etc.), and the term "chuck" includes all devices which secure a workpiece to a cutting machine. Step g) is portrayed in block 70 of FIG. 5 as "Mill Outside Surface Of Cosmetic Cover Blank". Step g) includes milling the outside surface 24 of the cosmetic cover blank 26.

Figure 5:
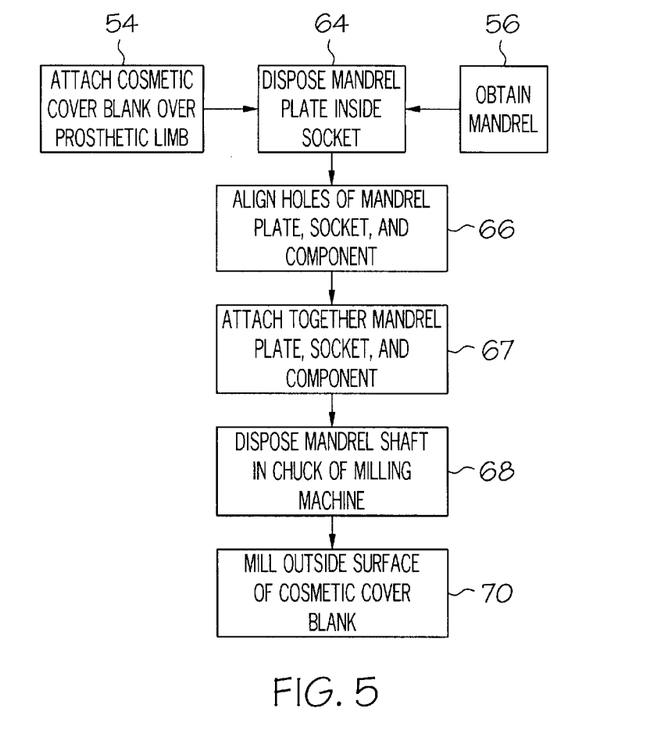
FIG. 5 is a block diagram of a first preferred method of the invention for fabricating a cosmetic cover for a prosthetic limb.

In an implementation of the first preferred method, step c) is performed after performing steps a) and b), step d) is performed after performing step c), step e) is performed after performing step d), step f) is performed after performing step e), and step g) is performed after performing step f). In another implementation, the prosthetic limb 12 is a prosthetic leg 72 including a prosthetic foot portion 74. In a further implementation, step f) includes disposing the mandrel shaft 58 in a chuck 42 of a computer-numerically-controlled milling machine 22. In one variation, after step g), there is included the step of applying a spray skin finish to the milled outer surface, and, in another variation, after step g), there is included the step of applying a cosmetic hose to the milled outside surface. In an additional implementation, the cosmetic cover blank 26 has a shape of a hollow tapered cylinder having a generally constant wall thickness, wherein the cosmetic cover blank 26 expands when heated, and wherein step a) includes heating the cosmetic cover blank 26, then sliding the cosmetic cover blank 26 over the prosthetic limb 12, and then applying a vacuum to draw the hot cosmetic cover blank 26 tight against the prosthetic limb 12.

A second preferred method of the invention is for fabricating a cosmetic cover 44 (shown in dashed line in FIG. 1) for a prosthetic limb 12. The prosthetic limb 12 has a socket 28 for placement over a wearer's residual limb 46, has a component 30 (such as, but not limited to, an interconnection component such as a pyramidal link plate) disposed exterior of the socket 28 (and optionally attachable to a prosthetic-limb element 76 such as a vertical shaft), and has a lock 32 disposed interior of the socket 28. The component 30 and the distal end 48 of the socket 28 have a plurality of aligned holes 50 and 52, wherein the holes 50 of the component 30 are threaded holes. The lock 32 has a plurality of threaded bolts 80 which are rotatable from inside the socket 28, which extend through the holes 52 of the socket 28, and which are engaged with the threaded holes of the component 30. The second preferred method includes steps a) through f). Step a) is portrayed in block 82 of FIG. 6 as "Attach Cosmetic Cover Blank Over Prosthetic Limb". Step a) includes attaching a cosmetic cover blank 26 over the prosthetic limb 12. Step b) is portrayed in block 84 of FIG. 6 as "Obtain Mandrel". Step b) includes obtaining a mandrel 40 having a mandrel shaft 58 and having a mandrel plate 60 attached to one end of the mandrel shaft 58, wherein the mandrel plate 60 has a plurality of holes 62 matching the holes of the socket 28. Step c) is portrayed in block 86 as "Remove Lock". Step c) includes removing the lock 32 from the component 30 and the socket 28 such as by disengaging the threaded bolts 80 from the threaded holes of the component 30 and then separating the lock 32 from the socket 28. Step d) is portrayed in block 88 of FIG. 6 as "Replace Removed Lock With Mandrel Plate And Threaded Fasteners". Step d) includes replacing the removed lock with the mandrel plate 60 and a plurality of threaded fasteners 90 which pass through the holes 62 and 52 of the mandrel plate 60 and the socket 28 and which engage the threaded holes of the component 30. Step e) is portrayed in block 92 of FIG. 6 as "Dispose Mandrel Shaft In Chuck Of Milling Machine". Step e) includes disposing the mandrel shaft 58 in a chuck 42 of a milling machine (such as, but not limited to, a CNC milling machine 22). Step f) is portrayed in block 94 of FIG. 6 as "Mill Outside Surface Of Cosmetic Cover Blank". Step f) includes milling the outside surface 24 of the cosmetic cover blank 26.

Figure 6:
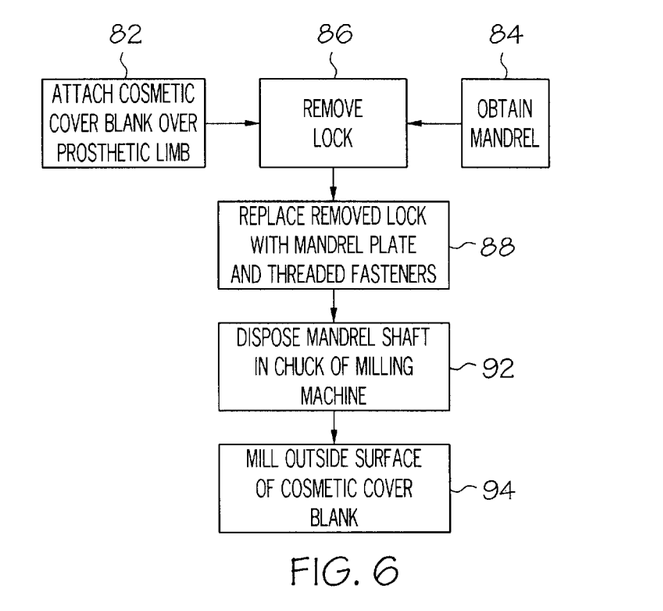
FIG. 6 is a block diagram of a second preferred method of the invention for fabricating a cosmetic cover for a prosthetic limb.

In an implementation of the second preferred method, step c) is performed after performing steps a) and b), step d) is performed after performing step c), step e) is performed after performing step d), and step f) is performed after performing step e. In another implementation, the prosthetic limb 12 is a prosthetic leg 72 including a prosthetic foot portion 74. In a further implementation, step f) includes disposing the mandrel shaft 58 in a chuck 42 of a computer-numerically-controlled milling machine 22. In one variation, after step f), there is included the step of applying a spray skin finish to the milled outer surface, and, in another variation, after step f), there is included the step of applying a cosmetic hose to the milled outside surface. In an additional implementation, the cosmetic cover blank 26 has a shape of a hollow tapered cylinder having a generally constant wall thickness, wherein the cosmetic cover blank 26 expands when heated, and wherein step a) includes heating the cosmetic cover blank 26, then sliding the cosmetic cover blank 26 over the prosthetic limb 12, and then applying a vacuum to draw the hot cosmetic cover blank 26 tight against the prosthetic limb 12.

Figure 2:
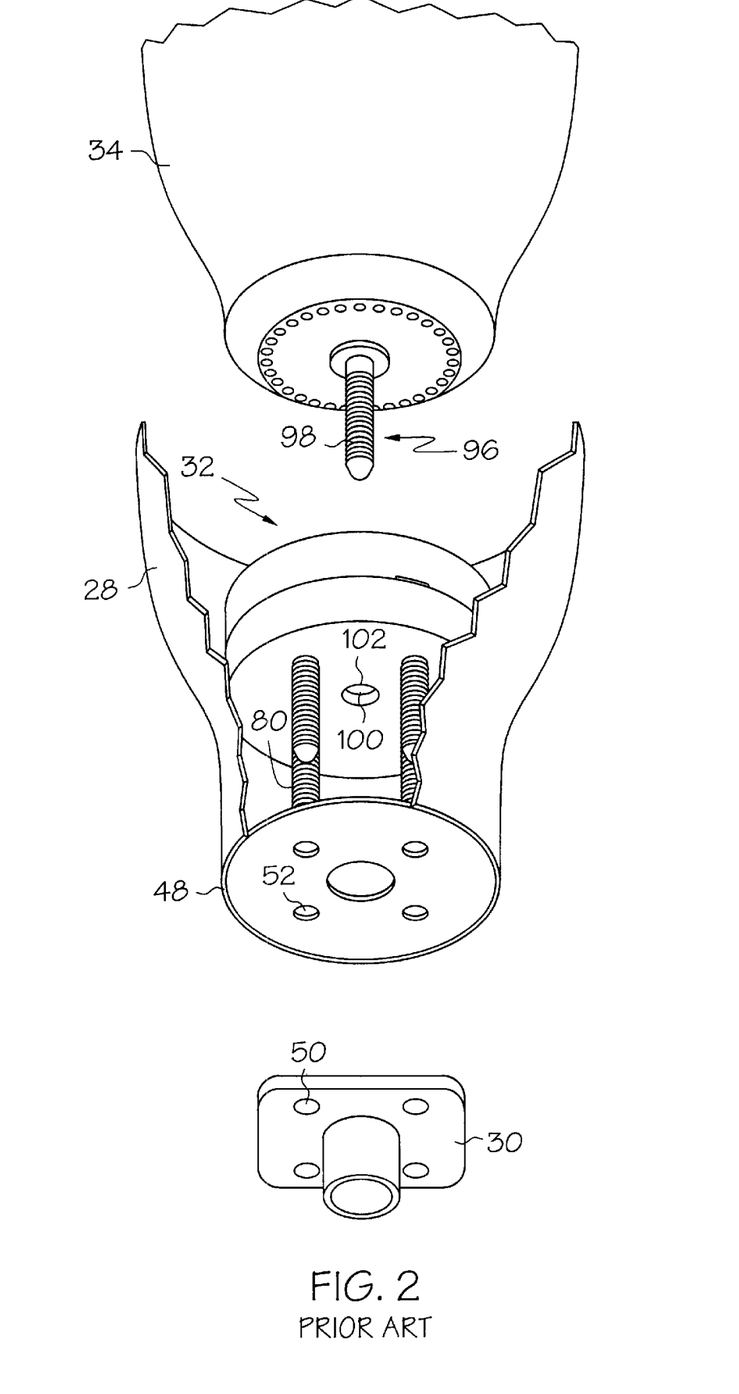
FIG. 2 is an exploded, partially cut-away, prior-art view of an inner sleeve, a socket, a lock, and a component of the removed prosthetic leg of FIG. 1.

In an exemplary implementation of the second preferred method, before step a), there are included the sequential steps of: fitting the prosthetic limb 12 to the wearer's residual limb 46; adjusting the prosthetic limb 12; and removing the prosthetic limb 12 from the wearer's residual limb 46. Preferably, the lock 32 has a substantially cylindrical shape having a diameter, and the mandrel plate 60 has a substantially cylindrical shape having a diameter substantially equal to the diameter of the lock 32. As best seen in FIG. 2, the prosthetic limb 12 includes an inner sleeve 34 for engaging a wearer's residual limb 46, and the inner sleeve 34 has a locking pin 96 with teeth 98. The lock 32 has a channel 100 for receiving the locking pin 96 and has a releaseable projection 102 extending into the channel 100 for engaging the locking pin 96 between adjacent teeth 98. Typically, when the prosthetic limb 12 is a prosthetic leg 72, before step a) there is included the step of detaching the prosthetic foot portion 74 of the prosthetic leg 72, and before step f) there is included the step of reattaching the prosthetic foot portion 74. The prosthetic foot portion 74 is preferably detached since its offset center of gravity could impart instability to the rotating workpiece. Preferably, step f) includes milling the outside surface 24 of the cosmetic cover blank 26 with a computer-numerically-controlled milling machine 22 using a mirror image of digital dimensions derived from measurements of a sound limb 14.

The methods of the invention fabricate a cosmetic cover for a prosthetic limb when the prosthetic limb has been removed from a wearer and while a cosmetic cover blank is attached to the prosthetic limb. The mandrel plate provides a secured attachment of the mandrel to the prosthetic limb and hence to the cosmetic cover blank attached to the prosthetic limb, and the mandrel shaft provides a secured attachment of the mandrel to the chuck of a milling machine. Such methods of the invention avoid the labor-intensive manual carving steps of some conventional methods.

Figure 3:
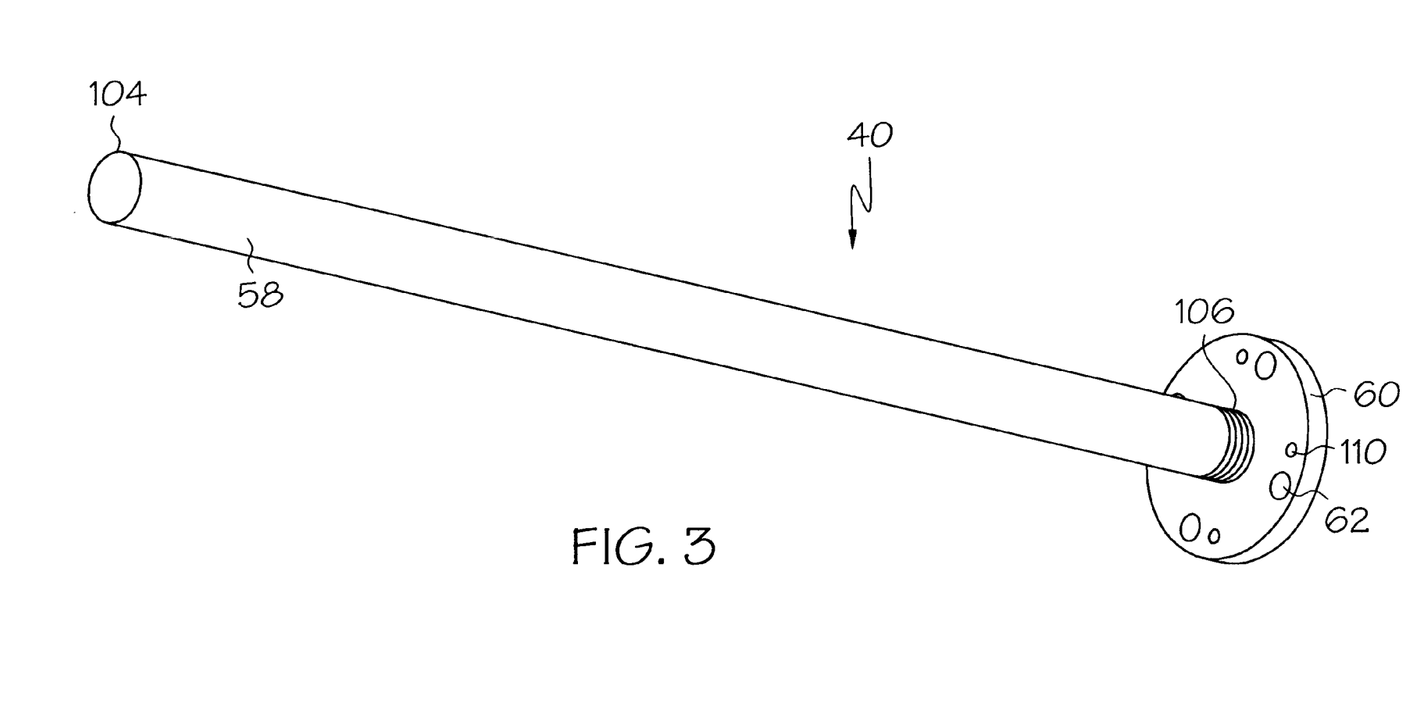
FIG. 3 is a perspective view of a preferred embodiment of the mandrel of the invention.
Figure 4:
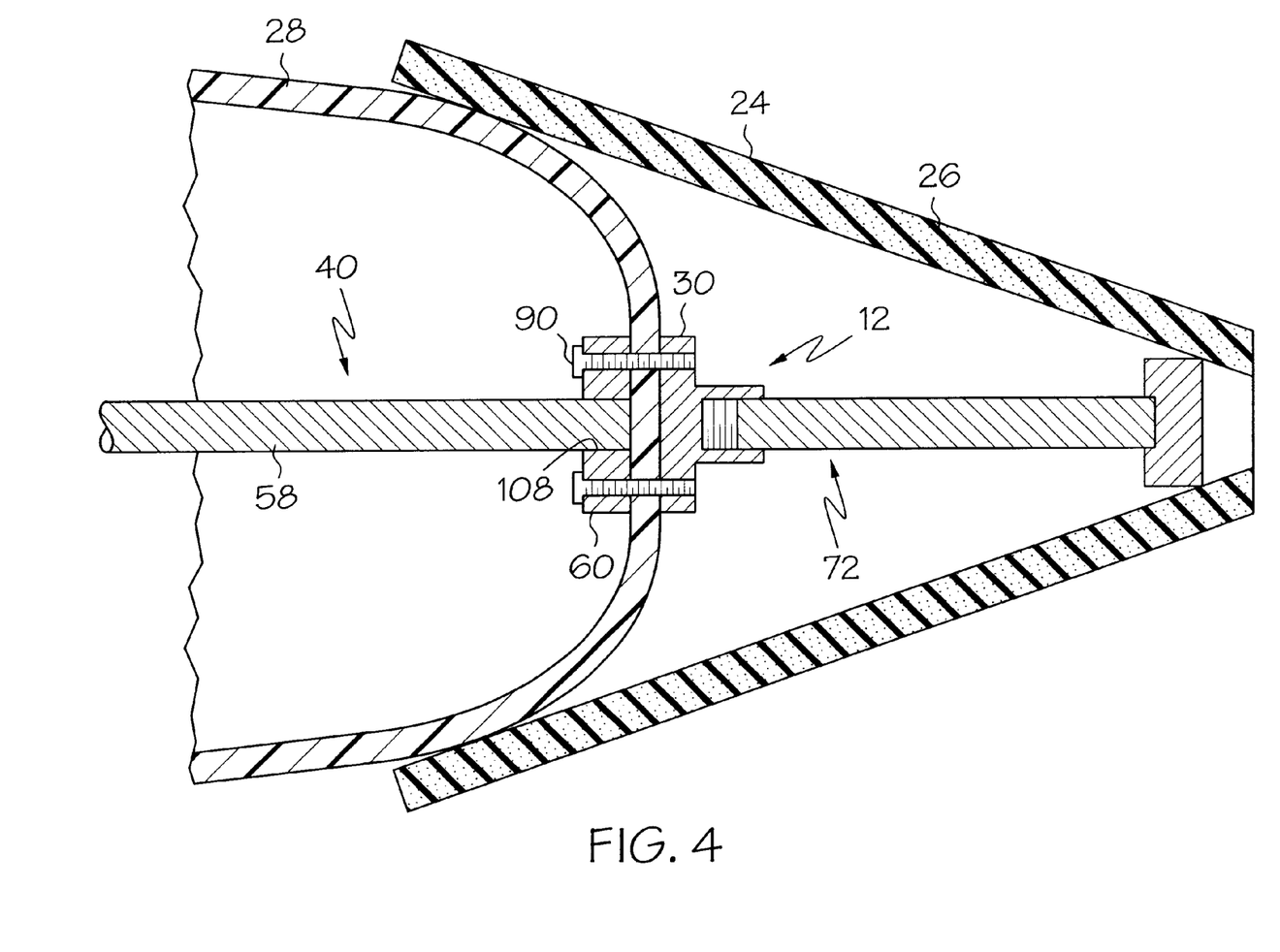
FIG. 4 is a sectional view of a cosmetic cover blank attached to the removed prosthetic leg of FIG. 1 and of the mandrel of FIG. 3 attached to the socket and the component, wherein the prosthetic foot portion has been removed, and wherein the longitudinal axis of the socket lies in the cutting plane.

A first expression of a preferred embodiment of the invention is for a mandrel 40 for supporting, in a milling machine (such as, but not limited to, a CNC milling machine 22), a cosmetic cover blank 26 attached to a prosthetic limb 12 during milling of an outside surface 24 of the cosmetic cover blank 26. The prosthetic limb 12 has a socket 28 for placement over a wearer's residual limb 46 and has a component 30 (such as, but not limited to, a pyramidal link plate) disposed exterior of the socket 28, wherein the component 30 and the distal end 48 of the socket 28 have a plurality of alignable holes 50 and 52 for attachment of the component 30 to the socket 28. The mandrel 40 includes a mandrel shaft 58 and a mandrel plate 60 attachable to the shaft 58. The mandrel shaft 58 has a first end 104 for placement in a chuck 42 of the milling machine and has a second threaded end 106. The mandrel plate 60 has a threaded hole 108 for engagement with the second threaded end 106 of the mandrel shaft 58 and has a plurality of holes 62, in a conventional four-hole pattern, matching the holes 52 of the socket 28, wherein the mandrel plate 60 is attachable to the component 30 from within the socket 28 through the holes 62 of the mandrel plate 60, the holes 52 of the socket 28, and the holes 50 of the component 30. Preferably, the second threaded end 106 of the mandrel shaft 58 is engaged in the threaded hole 108 of the mandrel plate 60. In one design, the mandrel plate 60 also has a multiplicity of additional holes 110 matching a second conventional four-hole pattern.

A second expression of a preferred embodiment of the invention is for a mandrel 40 for supporting, in a milling machine (such as, but not limited to, a CNC milling machine 22), a cosmetic cover blank 26 attached to a prosthetic limb 12 during milling of an outside surface 24 of the cosmetic cover blank 26. The prosthetic limb 12 has a socket 28 for placement over a wearer's residual limb 46, has a component 30 (such as, but not limited to, an interconnection component such as a pyramidal link plate) disposed exterior of the socket 28 (and optionally attachable to a prosthetic-limb element 76 such as a vertical shaft), and has a lock 32 disposed interior of the socket 28, wherein the component 30 and the distal end 48 of the socket 28 have a plurality of alignable holes 50 and 52, wherein the holes 50 of the component 30 are threaded holes, and wherein the lock 32 has a plurality of threaded bolts 80 which are rotatable from inside the socket 28, which are disposable to extend through the holes 52 of the socket 28, and which are engageable with the threaded holes of the component 30 for attachment of the component 30 to the socket 28. The mandrel 40 includes a mandrel shaft 58 and a mandrel plate 60. The mandrel shaft 58 has a first end 104 for placement in a chuck 42 of the milling machine and having a second threaded end 106. The mandrel plate 60 has a threaded hole 108 for engagement with the second threaded end 106 of the mandrel shaft 58 and has a plurality of holes 62 matching the holes 52 of the socket 28, wherein the mandrel plate 60 is attachable to the component 30 from within the socket 28 through the holes 62 and 52 of the mandrel plate 60 and the socket 28 and the threaded holes of the component 30. In one design, the lock 32 has a substantially cylindrical shape having a diameter, and the mandrel plate 60 has a substantially cylindrical shape having a diameter substantially equal to the diameter of the lock 32. Preferably, the second threaded end 106 of the mandrel shaft 58 is engaged in the threaded hole 108 of the mandrel plate 60. In another design, the mandrel plate 60 also has a multiplicity of additional holes 110 matching holes of a different socket of a different prosthetic limb.

The preferred embodiment of the mandrel of the invention provides a mandrel plate and a mandrel shaft, wherein the mandrel plate securely attaches the mandrel to the prosthetic limb and hence to the cosmetic cover blank attached to the prosthetic limb, and wherein the mandrel shaft securely attaches the mandrel to the chuck of a milling machine. This allows fabrication of a cosmetic cover for a prosthetic limb when the prosthetic limb has been removed from a wearer and while a cosmetic cover blank is attached to the prosthetic limb. Such fabrication avoids the labor-intensive manual carving steps of some conventional methods.

As can be appreciated by the artisan, successful milling of the outside surface of the cosmetic cover blank for a prosthetic limb, such as a prosthetic leg, requires proper orientation of the prosthetic limb in the CNC milling machine. The controlling software of the milling machine needs to be aware of the location of the distal surface of the cosmetic cover blank, the distal end of the socket, and the orientation of the prosthetic limb when mounted in the chuck of the milling machine. These locations and orientations can be manually located by moving the cutter to these locations, and coordinating these locations with prompts from the software interface.

The desired outside surface data for a finished cosmetic cover can be collected in a variety of ways. One method is to adjust the circumferential and length dimensions of a cosmetic cover template within the software. Another method is to digitize the sound limb and produce a mirror-image file. In either case, both the orientation of the cosmetic cover and the height location of the cosmetic cover must be such that it mimics the sound side as a mirror image (i.e., certain landmarks may be entered in the software indicating the location of the patella, the location of the distal surface of the socket, the location of the proximal surface of the prosthetic foot portion and, as required, the orientation of the patella).

On a finished cosmetic cover, the proximal portion of the cosmetic cover is usually thin as the cosmetic cover begins to transition into the proximal outside surface of the socket. Therefore, the location of the socket and its geometry are critical to preventing the cutting tool from striking the socket. The geometry of the inside surface of the socket usually is already available since it was the file that typically was used to produce the modified model of the patient's limb for socket fabrication. However, the artisan must be aware of the socket thickness. This thickness can be determined in a number of ways. One way is to use the methods described in U.S. Pat. No. 5,901,060. Another method is to measure the thickness of the socket prior to affixing the cosmetic cover blank to the socket. In one procedure, this thickness is applied globally to the inside surface data to suggest the added thickness of the socket, and the orientation is obtained from the orientation of the model that was set originally when carving the positive modified model for socket fabrication.

The proximal geometry of any prosthetic foot portion is obtainable by using the digitizing tool. This information typically is gathered when collecting other orientation and location landmarks as described in the above paragraphs.

The foregoing description of several methods and several expressions of a preferred embodiment of the invention have been presented for purposes of illustration. It is not intended to be exhaustive or to limit the invention to the precise form and processes disclosed, and obviously many modifications and variations are possible in light of the above teaching. It is intended that the scope of the invention be defined by the claims appended hereto.

What is claimed:

1. A method for fabricating a cosmetic cover for a prosthetic limb, the prosthetic limb having a socket for placement over a wearer's residual limb and having a component disposed exterior of the socket, the component and the distal end of the socket having a plurality of alignable holes for attachment of the component to the socket, wherein the method comprises the steps of:

a) attaching a cosmetic cover blank over the prosthetic limb;

b) obtaining a mandrel having a mandrel shaft and having a mandrel plate attached to one end of the mandrel shaft, wherein the mandrel plate has a plurality of holes matching the holes of the socket;

c) disposing the mandrel plate inside the socket;

d) aligning the holes of the mandrel plate, the socket, and the component;

e) attaching together the mandrel plate, the socket, and the component through the holes of the mandrel plate, the socket, and the component;

f) disposing the mandrel shaft in a chuck of a milling machine; and g) milling the outside surface of the cosmetic cover blank.

2. The method of claim 1, wherein the prosthetic limb is a prosthetic leg including a prosthetic foot portion.

3. The method of claim 1, wherein step f) includes disposing the mandrel shaft in a chuck of a computer-numerically-controlled milling machine.

4. The method of claim 1, wherein, after step g), there is included the step of applying a spray skin finish to the milled outside surface.

5. The method of claim 1, wherein, after step g), there is included the step of applying a cosmetic hose to the milled outside surface.

6. The method of claim 1, wherein the cosmetic cover blank has a shape of a hollow tapered cylinder having a generally constant wall thickness, wherein the cosmetic cover blank expands when heated, and wherein step a) includes heating the cosmetic cover blank and then sliding the cosmetic cover blank over the prosthetic limb.

7. A method for fabricating a cosmetic cover for a prosthetic limb, the prosthetic limb having a socket for placement over a wearer's residual limb, having a component disposed exterior of the socket, and having a lock disposed interior of the socket, wherein the component and the distal end of the socket have a plurality of aligned holes, wherein the holes of the component are threaded holes, wherein the lock has a plurality of threaded bolts which are rotatable from inside the socket, which extend through the holes of the socket, and which are engaged with the threaded holes of the component, and wherein the method comprises the steps of:

a) attaching a cosmetic cover blank over the prosthetic limb;

b) obtaining a mandrel having a mandrel shaft and having a mandrel plate attached to one end of the shaft, wherein the mandrel plate has a plurality of holes matching the holes of the socket;

c) removing the lock from the component and the socket;

d) replacing the removed lock with the mandrel plate and a plurality of threaded fasteners which pass through the holes of the mandrel plate and the socket and which engage the threaded holes of the component;

e) disposing the mandrel shaft in a chuck of a milling machine; and f) milling the outside surface of the cosmetic cover blank.

8. The method of claim 7, wherein, before step a), there are included the sequential steps of: fitting the prosthetic limb to the wearer's residual limb; adjusting the prosthetic limb; and removing the prosthetic limb from the wearer's residual limb.

9. The method of claim 8, wherein the lock has a substantially cylindrical shape having a diameter and wherein the mandrel plate has a substantially cylindrical shape having a diameter substantially equal to the diameter of the lock.

10. The method of claim 9, wherein the prosthetic limb includes an inner sleeve for engaging a wearer's residual limb, wherein the inner sleeve has a locking pin with teeth, wherein the lock has a channel for receiving the locking pin, and wherein the lock has a releaseable projection extending into the channel for engaging the locking pin between adjacent teeth.

11. The method of claim 10, wherein the prosthetic limb is a prosthetic leg including a prosthetic foot portion.

12. The method of claim 11, wherein the cosmetic cover blank has a shape of a hollow tapered cylinder having a generally constant wall thickness, wherein the cosmetic cover blank expands when heated, and wherein step a) includes heating the cosmetic cover blank and then sliding the cosmetic cover blank over the prosthetic limb.

13. The method of claim 12, wherein, before step a), there is included the step of detaching the prosthetic foot portion of the prosthetic leg and wherein, before step f), there is included the step of reattaching the prosthetic foot portion.

14. The method of claim 13, wherein step e) includes disposing the mandrel shaft in a chuck of a computer-numerically-controlled milling machine.

15. The method of claim 14, wherein step f) includes milling the outside surface of the cosmetic cover blank with the computer numerically controlled machine using digital dimensions derived from measurements of a sound limb.

16. The method of claim 15, wherein, after step f), there is included the step of applying a spray skin finish to the milled outside surface.

17. The method of claim 15, wherein, after step f), there is included the step of applying a cosmetic hose to the milled outside surface.

* * * * *